(12) United States Patent
Rochat et al.

(10) Patent No.: US 9,487,254 B2
(45) Date of Patent: Nov. 8, 2016

(54) VEHICLE AND METHOD FOR THE INDEPENDENT INSPECTION OF HARD-TO-REACH INNER SPACES

(75) Inventors: Frederic Rochat, Chavannes-les-Forts (CH); Patrick Schoeneich, Brent (CH); Francesco Mondada, Bussigny (CH); Roland Richard Moser, Zurich (CH)

(73) Assignee: General Electric Technology GmbH, Baden (CH)

( * ) Notice: Subject to any disclaimer, the term of this patent is extended or adjusted under 35 U.S.C. 154(b) by 40 days.

(21) Appl. No.: 12/950,381

(22) Filed: Nov. 19, 2010

(65) Prior Publication Data
US 2011/0174565 A1 Jul. 21, 2011

(30) Foreign Application Priority Data
Nov. 27, 2009 (CH) ........................................ 1823/09

(51) Int. Cl.
*B60L 13/04* (2006.01)
*B61C 15/04* (2006.01)
*B62D 57/024* (2006.01)
*G01M 5/00* (2006.01)
*G01M 11/08* (2006.01)
*G01N 35/04* (2006.01)

(52) U.S. Cl.
CPC .......... *B62D 57/024* (2013.01); *G01M 5/0033* (2013.01); *G01M 5/0075* (2013.01); *G01M 5/0091* (2013.01); *G01M 11/08* (2013.01); *G01N 2035/0489* (2013.01)

(58) Field of Classification Search
CPC ..... B60L 13/04; B60B 39/00; B60B 19/006; Y10S 901/01; Y10S 901/50; Y10S 180/901; B60Y 2200/47; B62D 57/024; B62D 55/265; F16L 55/32; B63B 59/10; B63B 2231/30; B23K 37/0264; B61C 15/04
USPC .................................................... 180/167, 218
See application file for complete search history.

(56) References Cited

U.S. PATENT DOCUMENTS 3,609,612 A * 9/1971 Tibbling ................. B63B 59/10
114/222
4,592,699 A 6/1986 Maierbacher
4,772,042 A * 9/1988 Jinsheng ................. B60G 3/28
280/124.109
(Continued)

FOREIGN PATENT DOCUMENTS

DE 29808730 U1 8/1998
EP 0005616 A1 11/1979
(Continued)

OTHER PUBLICATIONS

Office action issued from Japanese Patent Office dated Aug. 12, 2014 for JP Application No. 2010-265588.

*Primary Examiner* — Bryan Evans
(74) *Attorney, Agent, or Firm* — GE Global Patent Operation; Cynthia W. Flanigan

(57) ABSTRACT

A vehicle is provided for the independent inspection of hard-to-reach inner spaces which are bounded by ferromagnetic inner walls, especially in large cast parts, such as steam chests of a steam turbine. The vehicle includes at least two wheels which are rotatable around a common axis, are at a distance from each other in the axial direction, and can be driven independently of each other. With such a vehicle, the entire inner space can be inspected if the vehicle has adherence elements which hold the vehicle against the gravity force with the wheels on the respective inner wall.

18 Claims, 4 Drawing Sheets

(56) References Cited

U.S. PATENT DOCUMENTS

| | | | |
|---|---|---|---|
| 5,220,869 A * | 6/1993 | Pelrine et al. | 105/78 |
| 5,388,528 A | 2/1995 | Pelrine et al. | |
| 5,809,099 A * | 9/1998 | Kim et al. | 376/249 |
| 5,819,863 A | 10/1998 | Zollinger et al. | |
| 6,345,675 B1 | 2/2002 | Hueber | |
| 6,548,982 B1 * | 4/2003 | Papanikolopoulos | B62D 57/02 318/568.11 |
| 7,056,185 B1 * | 6/2006 | Anagnostou | 446/456 |
| 7,233,221 B2 * | 6/2007 | Reboredo Losada et al. | 335/302 |
| 2007/0235238 A1 * | 10/2007 | Sadegh et al. | 180/164 |
| 2008/0173593 A1 | 7/2008 | Coull et al. | |

FOREIGN PATENT DOCUMENTS

| | | |
|---|---|---|
| EP | 2003044 A1 | 12/2008 |
| JP | 62-26172 | 2/1987 |
| JP | 6-191400 | 7/1994 |
| JP | 09175454 A * | 7/1997 |
| JP | 10-151586 | 6/1998 |
| WO | 0128797 A1 | 4/2001 |

* cited by examiner

VEHICLE AND METHOD FOR THE INDEPENDENT INSPECTION OF HARD-TO-REACH INNER SPACES

FIELD OF INVENTION

The present invention relates to the field of inspection of components with hard-to-reach inner spaces. It refers to a vehicle for the independent inspection of hard-to-reach inner spaces.

BACKGROUND

The inspection of large plants for power generation, such as gas or steam turbines, is of great interest in order to detect damage in time and to minimize the downtime of such plants.

Particularly large cast parts of these plants, such as steam chests, i.e. the structures which connect the live steam feed lines to the steam turbine and contain all the necessary valves (see, for example, EP-A1-0 005 616 or U.S. Pat. No. 4,592,699) frequently display crack formation because they are exposed to high pressures and temperatures. If such a crack formation is detected in time, that is to say at an early stage, suitable measures can be initiated and therefore serious consequences avoided.

Whereas an inspection on the outer side of such structures is comparatively simple, the inspection of the inner walls becomes more difficult due to the fact that the access openings to the inner spaces, in comparison to the inner spaces themselves, are often very narrow and that the inner walls have irregular, especially concave, shapes which restrict the space for an inspection device which is introduced into the inner space.

SUMMARY

The present disclosure is directed to a vehicle for independent inspection of inner spaces, which are bounded by ferromagnetic inner walls, in cast parts. The vehicle includes at least two wheels which are rotatable around a common axis, are at a distance from each other in an axial direction and can be driven independently of each other. The vehicle further includes adherence elements which hold the vehicle against a force of gravity with the wheels on the respective inner wall.

In another aspect, the disclosure is directed to a method for independently inspecting inner spaces, which are bounded by ferromagnetic inner walls, in steam chests of steam turbines. The method includes introducing a vehicle into the inner space, the vehicle includes at least two wheels which are rotatable around a common axis, are arranged at a distance from each other in an axial direction and can be driven independently of each other. The vehicle also includes adherence elements which hold the vehicle against a force of gravity with the at least two wheels on the respective inner wall.

BRIEF DESCRIPTION OF THE DRAWINGS

The invention shall be explained in more detail in the following, based on exemplary embodiments in conjunction with the drawing. In the drawing

DETAILED DESCRIPTION OF THE PREFERRED EMBODIMENTS

Introduction to the Embodiments

Figure 1:
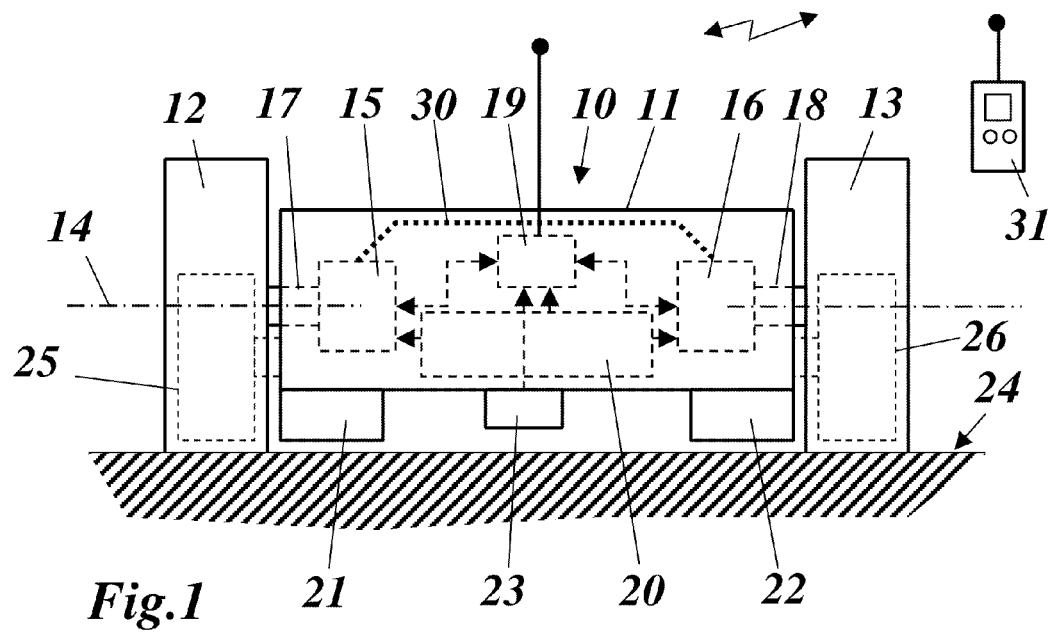
FIG. 1 shows in a side view perpendicular to the axis an inspection vehicle according to an exemplary embodiment of the invention.

It is therefore an object of the invention to create a device which can be advantageously used for the inspection of inner spaces or inner walls in such structures, and which, includes low space requirement and good maneuverability, is suitable for a multiplicity of inspection types and without any problem can be moved along inner walls of any spatial orientation.

The object is achieved by means of the entirety of the features of claim 1. The invention proposes a vehicle which comprises at least two wheels which are rotatable around a common axis, are at a distance from each other in the axial direction, and can be driven independently of each other, and has adherence elements, especially magnetic elements, which hold the vehicle against force of gravity with the wheels on the respective inner wall.

The single-axis construction enables the vehicle to be introduced in the axial direction through restricted openings into the inner space which is to be inspected. In the inner space, it can be maneuvered and moved in any direction on account of the two driven wheels, wherein on vertical walls or in overhead mode it can be kept in contact with the respective wall by adherence elements, preferably by magnetic forces.

Single-axis vehicles with two separately driven wheels, taken alone, have been known for a long time. DE-U1-298 08 730 discloses a mobile device with two wheels and one wheel axis and a basic body which is mounted in an oscillating manner on the wheel axis and for example may be a vehicle cab. The driving of the wheels is carried out by means of an electric motor or internal combustion engine via a central differential transmission and two differentials which are associated with the wheels.

A single-axis vehicle with two independently driven wheels is known from W0-A1-01/28797 (see, for example, FIG. 1 there), in which steering is effected by means of different rotational speeds of the wheels and a low center of gravity ensures the progressive motion of the vehicle.

A remote-controlled single-axis cross-country vehicle, which is equipped with wheels which act in all directions and therefore has a very costly and susceptible mechanical system, is known from U.S. Pat. No. 7,056,185 B1.

In US-A1-2008/0173493, a two-wheeled robot is described, wherein the controlling of the driven wheels, which is necessary for the operation, is expressly dealt with.

Finally, under the trade-name Recon Scout®, a single-axis, two-wheeled miniaturized mobile robot is known, which in a remote-controlled manner in a hostile or hazardous environment can take pictures with an installed video camera and transmit the pictures to a receiver. The robustly constructed robot has plastic wheels between which a cylindrical housing consisting of titanium is arranged, in which the camera, the drive and the control unit are accommodated. A flexible "stabilizing tail", which prevents rotation of the housing during forward travel, is attached on the housing on the outside. Such a robot has an exemplary wheel diameter of about 8 cm, a length in the axial direction of about 19 cm, and a weight of about 0.5 kg.

The vehicle according to the invention stands out from these known single-axis, two-wheeled vehicles by the fact that it includes adherence elements, especially magnetic elements, by which it can also be held on vertical or overhead walls comprised of ferromagnetic material so that its wheels do not lose contact with the wall. It is self-evident in this case that the adherence elements or magnetic elements have to be sufficiently powerful in order to hold the vehicle, together with its installed (optical or otherwise) inspection devices, against the force of gravity overhead on an inner wall.

In principle, an adhering effect can be achieved by vacuum (suction) or an adhesive. According to one development of the invention, the adherence elements or magnetic elements, however, comprise at least one permanent magnet. Provision is preferably made for at least two permanent magnets which are associated with the individual wheels. The permanent magnets can especially be arranged partially or completely in the wheels for protection against outside influences. As a result of this, the advantage is additionally created of the permanent magnets being accurately placed where contact between wheel and wall has to be maintained, which has a favorable effect especially in the case of uneven walls. With correspondingly designed permanent magnets, large holding forces can be achieved without power having to be made available in the vehicle for this.

According to another development, the permanent magnets are decoupled from the wheels of the vehicle. The decoupling ensures that the permanent magnets remain oriented towards the wall if the wheels are rotated or can be oriented towards another wall (in a space corner) without the wheels having to be moved.

The independent driving of the wheels can basically be achieved by corresponding differential arrangements, as is described in printed publication DE-U1-298 08 730 which is referred to in the introduction. According to one development of the invention, a separate drive is associated with each of the wheels, however, and the drives are supplied with power from an energy storage which is accommodated in the vehicle and are controlled by a control unit which is accommodated in the vehicle. As a result of this, large mobility of the vehicle can be achieved with low constructional cost. As an energy storage, especially a battery or an accumulator comes into consideration.

It is quite conceivable within the scope of the invention for the vehicle to be controlled from the outside via a control line and for the inspection results to be transmitted also to the outside via this control line. In order to enable an unrestricted maneuverability for the vehicle, however, it is advantageous if the control unit can receive control commands from the outside wirelessly. The inspection results are then correspondingly transmitted in a wireless manner to the outside or are stored in the vehicle for later evaluation.

An improved adaptation of the vehicle to an uneven base surface can be achieved according to a further development by the at least two wheels being interconnected by an elastically flexible cross-member which acts as a spring suspension.

In order to protect the devices which are accommodated in the vehicle, such as drive and control unit, in a space-saving manner, the vehicle according to another development has a preferably cylindrical housing which extends between the wheels in the axial direction.

For inspection and/or control purposes, at least one sensor, i.e.: camera, optical sensor, electric sensor, electromagnetic sensor, ultrasonic sensor, or the like, is arranged on the vehicle. A video camera (with corresponding lighting by an incorporated light source) can be used in this case not only for optical detection of the state of the wall, but also for detecting the path of travel. Other sensors, which operate for example with ultrasound or eddy currents, can be used for crack detection or for non-destructive material testing.

DETAILED DESCRIPTION

In FIG. 1, in a side view perpendicular to the axis, an inspection vehicle according to an exemplary embodiment of the invention is reproduced. The vehicle 10 is formed as a single-axis vehicle and has two wheels 12 and 13 which are rotatably mounted around a common axis 14 and are at a distance from each other along the axis 14. The wheels 12, 13 preferably consist of a material, for example a plastic material, which has no magnetic screening effect. The material can be selected so that the wheels can have sufficient grip on the base surface, which is provided for them, of an inner wall 24 of a cast body. The outer circumference of the wheels 12, 13, however, may be provided with a corresponding coating or may have elements, such as transverse ribs, which bring about improved grip.

A housing 11, in which the devices which are required for driving and controlling the vehicle 10 are accommodated in a protected manner, extends between the two wheels 12, 13. The housing 11 is preferably cylindrical in order to be able to glide more easily over uneven surfaces when in use. So that the vehicle 10 bears with its wheels in any position on the inner wall 24 which consists of ferromagnetic material, on the underside of the housing two powerful permanent magnets 21, 22 are arranged in each case in direct proximity of one of the wheels 12, 13. As a result of this arrangement of the permanent magnets 21, 22, it is ensured that the housing 11 always remains stable in the same orientation to the inner wall 24, even if the wheels 12, 13 are rotated forwards or backwards.

Each of the two wheels 12, 13 is driven via a separate drive shaft 17 or 18 by a separate drive 15 or 16 which comprises an electric motor and is supplied with power from an energy storage 20. As a result of this, the wheels 12, 13 can execute any rotational movements independently of each other and therefore steer the vehicle in the desired direction or turn it on the spot. Instead of the two drives 15, 16, however, a single drive may also be used, wherein the wheels are then decoupled from each other by corresponding differential devices. Each wheel 12, 13, together with the drive shaft 17, 18 and the drive 15, 16, forms a unit. If the two units or drives are mechanically interconnected by an elastically flexible cross-member 30, which is then anchored on the housing, a spring suspension is created for the vehicle 10, which improves the handling characteristic.

The drives 15, 16, and therefore the movement direction and speed of the vehicle 10, are controlled by a control unit 19 which receives commands from a remote control device 31 in a wireless manner and, if applicable, transmits inspection results to the outside. The control unit 19 can work in concert with position and acceleration sensors, which are arranged on the vehicle, in order to balance the vehicle 10. As a result of the permanent magnets 21, 22, the vehicle 10 already has a stable position, however, so that such controlling is not absolutely necessary.

Figure 2:
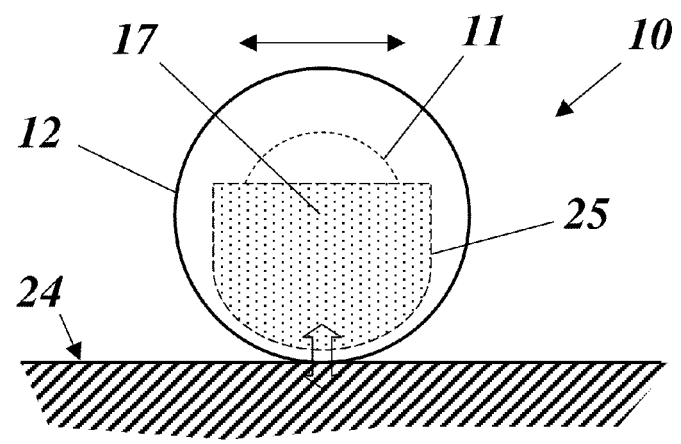
FIG. 2 shows the vehicle from FIG. 1 in a side view in the direction of the axis.
Figure 3A:
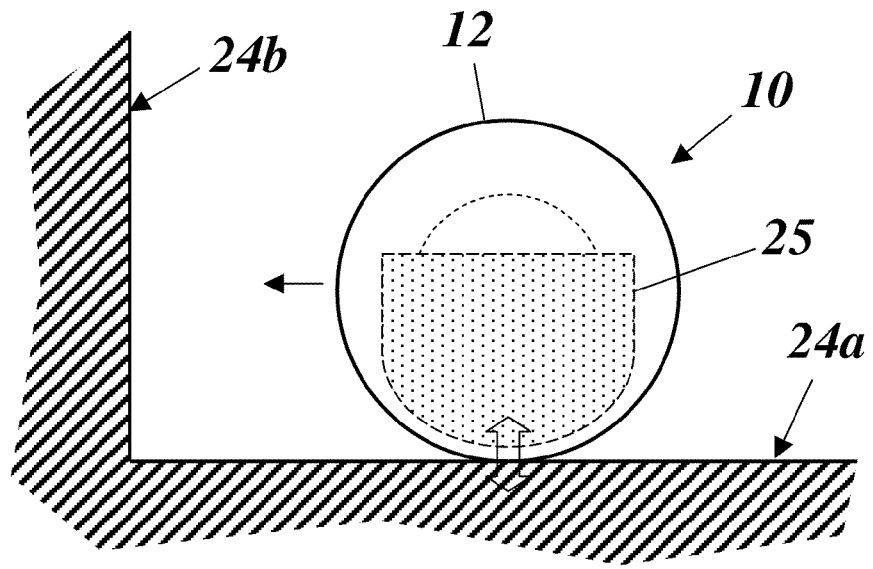
FIG. 3 shows in a plurality of sub-figures (3a to 3d) the movement sequence of the vehicle from FIG. 2 when passing round a rectangular space corner, and FIG. 4 schematically shows the introduction of the vehicle from FIG. 1 through a narrow opening into a widened inner space.
Figure 3B:
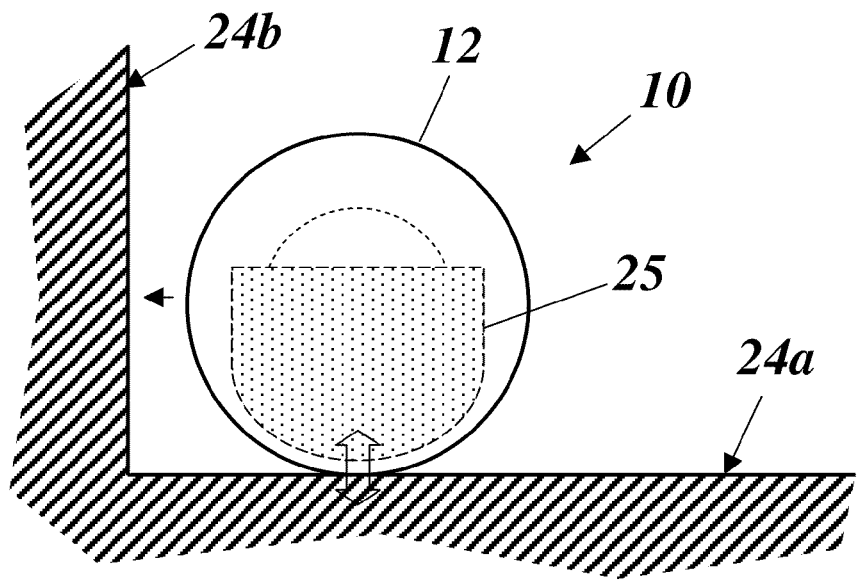
Figure 3C:
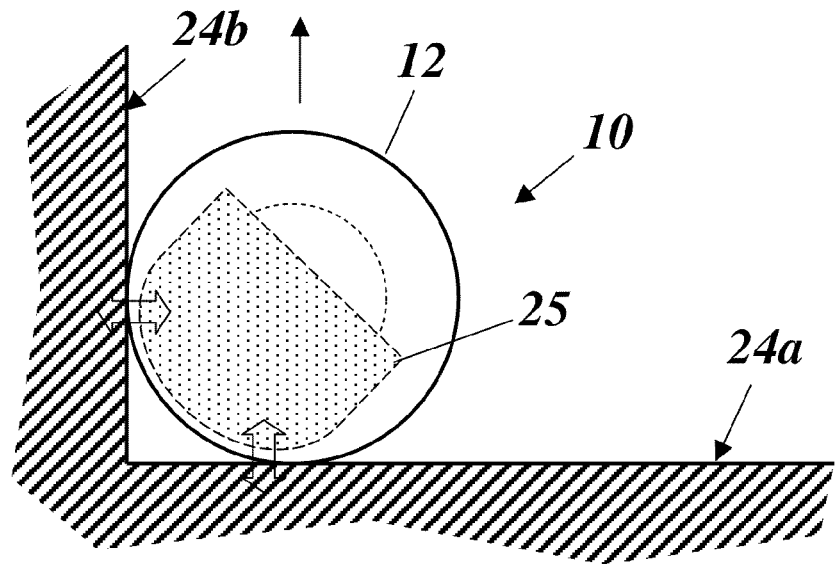
Figure 3D:
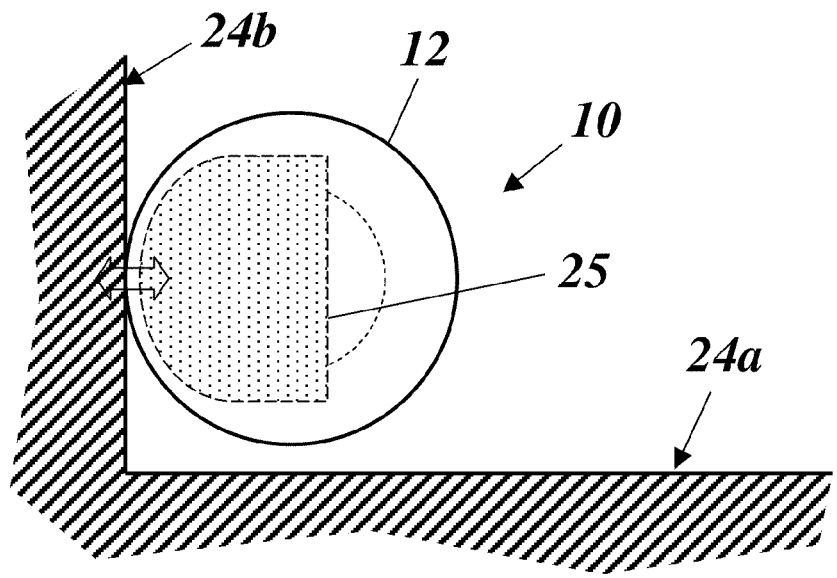

It is especially advantageous if instead of the exposed permanent magnets 21, 22 permanent magnets 25, 26 are provided in the wheels 12, 13. As a result of this, the permanent magnets 25, 26 on the one hand are protected against influences from outside (shocks, dust, magnetizable particles, etc.). On the other hand, the attracting magnetic forces are accurately concentrated also where the grip of the wheels 12, 13 is applied on the inner wall 24. The permanent magnets 25, 26 may have for example the semicircle-like edge contour which is shown in FIG. 2.

The construction of the vehicle 10 which is shown in FIG. 1 leads to the vehicle being able to travel in an inner space without any problem along space corners and to climb on vertical walls or move overhead on ceilings, as becomes clear from FIG. 3. In FIG. 3, a space corner is shown, at which two inner walls 24a, b of an inner space which is to be inspected abut at a right angle. As long as the vehicle 10 which is travelling on the horizontal inner wall 24a (the wheels rotate anticlockwise) is moving towards the vertical inner wall 24b (FIG. 3a, FIG. 3b), the permanent magnet 25, which is arranged asymmetrically to the axis 14, in the front wheel 12 (in the same way as the non-visible permanent magnet 26 in the rear wheel 13) points downwards and develops the maximum attractive force (double-arrow in FIGS. 3a, b), perpendicularly below the axis, with regard to the inner wall 24a lying beneath it.

If the vehicle 10 directly approaches the vertical inner wall 24b (FIG. 3c), the permanent magnet 25 is increasingly oriented in equal measure towards the horizontal and vertical inner wall 24a or 24b so that the vehicle 10 bears with its wheels 12, 13 on the two walls at the same time. If the wheels 12, 13 are then rotated further anticlockwise, the vehicle 10 travels vertically upwards on the vertical inner wall 24b, wherein the permanent magnet 25, with increasing distance from the horizontal inner wall 24a, is oriented exclusively towards the vertical wall 24b.

If the permanent magnets 21, 22 or 25, 26 are connected in a fixed manner to the housing 11, the housing 11 has a corresponding orientation towards the respective inner wall, upon the surface of which the vehicle 10 moves. If sensors 23 (cameras, crack detectors, etc; FIG. 1) are attached on the housing 11, these are oriented towards the wall surface in the same way. If the permanent magnets, however, are mounted in a freely pivotable manner around the axis 14, the housing 11, with the sensors 23 fastened thereupon, can be brought into an optionally adjustable position by a corresponding position control system with position sensors.

Figure 4:
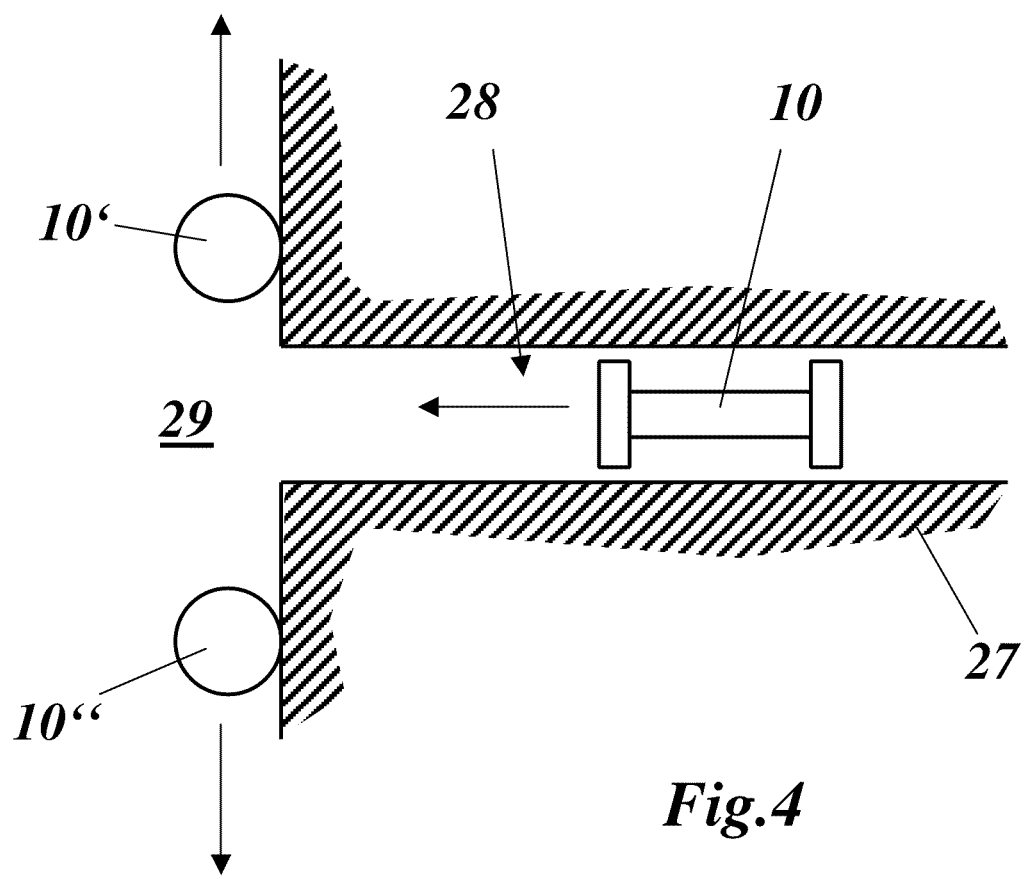

FIG. 4 schematically shows the introduction of the vehicle 10 from FIG. 1 through a narrow opening into a widened inner space 29. As a result of the favorable ratio of wheel diameter to axial length, the vehicle 10 can be introduced in axial orientation through a narrow bore 28 into the interior of a steam chest 27 or the like, in order to then travel, like the other vehicles 10' and 10", along the inner wall of the widened inner space 29 for inspection purposes. At the same time, it becomes clear from this that the inspection of a larger structure can be undertaken more quickly if a plurality of vehicles of the described type are used at the same time for the inspection. Furthermore, it is conceivable to mechanically couple together a plurality of vehicles of the described type to form a movable larger unit.

List of Designations 10, 10', 10" Inspection vehicle
11 Housing
12, 13 Wheel
14 Axis
15, 16 Drive
17, 18 Drive shaft
19 Control unit
20 Energy storage (for example battery)
21, 22 Permanent magnet
23 Sensor
24, 24a, b Inner wall
25, 26 Permanent magnet
27 Steam chest
28 Bore
29 Inner space
30 Cross-member (spring)
31 Remote control unit

What is claimed is:

1. A vehicle for independent inspection of ferromagnetic surfaces, the vehicle comprising:
    a housing having a single common axis passing therethrough;
    two wheels rotatable around the common axis arranged a distance from each other in an axial direction of the common axis adjacent opposed ends of the housing and operable to be driven independently of each other through separate common axis centered drive shafts and drives; and
    two permanent magnets arranged on an underside of the housing with each of the two permanent magnets abutting a different one of the opposed ends of the housing adjacent to each of the two wheels; and
    a separate adherence element enclosed within each of the two wheels to hold the wheels in engagement with the ferromagnetic surfaces,
    wherein the two wheels and the two permanent magnets are arranged to hold the housing stable in a fixed orientation with respect to a ferromagnetic surface upon motion of the two wheels on the ferromagnetic surface.

2. The vehicle as claimed in claim 1, wherein the adherence element in each wheel comprises at least one permanent magnet.

3. The vehicle as claimed in claim 2, wherein at least two permanent magnets are associated with the two wheels, respectively.

4. The vehicle as claimed in claim 1, wherein each of the drives is supplied with power from an energy storage which is accommodated in the vehicle, and each of the drives is controlled by a control unit which is accommodated in the vehicle.

5. The vehicle as claimed in claim 4, wherein the control unit receives control commands from outside the inner space wirelessly.

6. The vehicle as claimed in claim 1, wherein the two wheels are interconnected by an elastically flexible cross-member which acts as a spring suspension.

7. The vehicle as claimed in claim 1, wherein the housing is cylindrical.

8. The vehicle as claimed in claim 1, further comprising at least one sensor selected from the group consisting of: cameras, optical sensors, electric sensors, electromagnetic sensors and ultrasonic sensors accommodated with at least one of the two wheels.

9. A method for independently inspecting inner spaces bound by ferromagnetic surfaces, the method comprising:
    introducing a vehicle comprising a housing having a single common axis
    passing therethrough, and two wheels rotatable around the common axis with the two wheels arranged a distance from each other in an axial direction of the common axis adjacent opposed ends of the housing, into an inner space;

arranging two permanent magnets on an underside of the housing with each of the two permanent magnets abutting a different one of the opposed ends of the housing adjacent to each of the two wheels;

providing a separate adherence element enclosed within each of the two wheels to hold the wheels in engagement with the ferromagnetic surfaces; and driving each of the wheels independently of the other through separate common axis centered drive shafts and drives for inspection of inner spaces, wherein the two wheels and the two permanent magnets are arranged to hold the housing stable in a fixed orientation with respect to a ferromagnetic surface upon motion of the two wheels on the ferromagnetic surface.

10. The method of claim 9, wherein the adherence element in each wheel comprises at least one permanent magnet.

11. The method of claim 9, further comprising inspecting the inner wall using at least one sensor selected from the group consisting of: cameras, optical sensors, electric sensors, electromagnetic sensors and ultrasonic sensors, which is arranged on the vehicle.

12. The method of claim 9, further comprising controlling the vehicle from outside the inner space wirelessly.

13. The method of claim 11, further comprising transmitting data obtained by the at least one sensor to outside the inner space wirelessly.

14. The vehicle as claimed in claim 1, wherein the adherence element enclosed within each wheel is decoupled from the wheel of the vehicle so that the wheel may rotate on the common axis relative to the adherence element remaining oriented towards the inner wall.

15. The method as claimed in claim 9, wherein the adherence element enclosed within each wheel is decoupled from the wheel of the vehicle so that the wheel may rotate on the common axis relative to the adherence element remaining oriented towards the inner wall.

16. The vehicle as claimed in claim 7, wherein the housing is cylindrical and a diameter of the cylindrical housing is less than a diameter of either of the two wheels.

17. The vehicle as claimed in claim 1, wherein the adherence element enclosed within each wheel is arranged asymmetrically to the common axis.

18. The vehicle as claimed in claim 3, wherein the at least two permanent magnets have a circumference to engage a wall at least perpendicular to the ferromagnetic surface also engaged.

* * * * *

UNITED STATES PATENT AND TRADEMARK OFFICE
CERTIFICATE OF CORRECTION

PATENT NO. : 9,487,254 B2  
APPLICATION NO. : 12/950381  
DATED : November 8, 2016  
INVENTOR(S) : Rochat et al.

Page 1 of 1

It is certified that error appears in the above-identified patent and that said Letters Patent is hereby corrected as shown below:

On the Title Page

In Item (75), under "Inventors", in Column 1, Line 4, delete "Zurich" and insert -- Zürich --, therefor.

In the Specification

In Column 1, Line 64, delete "drawing. In the drawing" and insert -- drawings. In the drawings --, therefor.

In Column 2, Line 5, delete "corner," and insert -- corner; --, therefor.

In Column 2, Line 47, delete "W0-A1-01/28797" and insert -- WO-A1-01/28797 --, therefor.

In the Claims

In Column 6, Line 20, in Claim 1, delete "arranged a" and insert -- arranged at a --, therefor.

In Column 6, Line 65, in Claim 9, delete "axis" and insert -- axis; --, therefor.

In Column 6, Line 67, in Claim 9, delete "arranged a" and insert -- arranged at a --, therefor.

Signed and Sealed this  
Thirty-first Day of January, 2017

Michelle K. Lee  
*Director of the United States Patent and Trademark Office*